United States Patent [19]

Pagano

[11] Patent Number: 4,615,218
[45] Date of Patent: Oct. 7, 1986

[54] ULTRASONIC WHEEL PROBE WITH ACOUSTIC BARRIER

[76] Inventor: Dominick A. Pagano, 10 Sasqua Trail, Weston, Conn. 06883

[21] Appl. No.: 649,827

[22] Filed: Sep. 12, 1984

[51] Int. Cl.⁴ ............................................. G01N 29/04
[52] U.S. Cl. ...................................................... 73/639
[58] Field of Search ............................ 73/639, 635, 625

[56] References Cited

U.S. PATENT DOCUMENTS

| | | | |
|---|---|---|---|
| 4,165,648 | 8/1979 | Pagano | 73/639 |
| 4,174,636 | 11/1979 | Pagano | 73/639 |
| 4,398,421 | 8/1983 | White | 73/644 |
| 4,437,332 | 3/1984 | Pittaro | 73/644 |

*Primary Examiner*—Anthony V. Ciarlante
*Attorney, Agent, or Firm*—Lieberman, Rudolph & Nowak

[57] ABSTRACT

An ultrasonic wheel probe of the type having a wheel-shaped container with an annular outer surface for rotating about an axis of rotation and rolling upon a specimen to be tested is provided with a plurality of transducers for transmitting and receiving ultrasonic acoustic energy, respectively. In accordance with the invention, an acoustic barrier is interposed between the transmitting and receiving transducers, and immersed in the coupling fluid, so as to isolate the transmitting and receiving transducers from one another. With this arrangement, echoes emanating from the interface, or surface, of the specimen being tested are prevented from reaching the receiving transducer. By eliminating the interface echo the only echoes received are from the back wall of the specimen under test or from anomalies within the specimen, thereby permitting testing from the front surface to the back wall of the specimen. The acoustic barrier is preferably installed on a yoke of the wheel probe so as to be displaceable in a substantially radial direction in response to the contour of the specimen being tested. The radial alignment of the acoustic barrier is maintained by a pair of shafts which extend through the yoke and have linear bearings interposed therein. A resilient element, such as a spring, is arranged to urge the acoustic barrier to its maximum extent from the axis of rotation. An additional transducer is arranged to communicate ultrasonically with the acoustic barrier so as to monitor its radial location at all times. The signals produced by this monitoring transducer can be utilized to control feedback and gate triggering circuitry.

23 Claims, 3 Drawing Figures

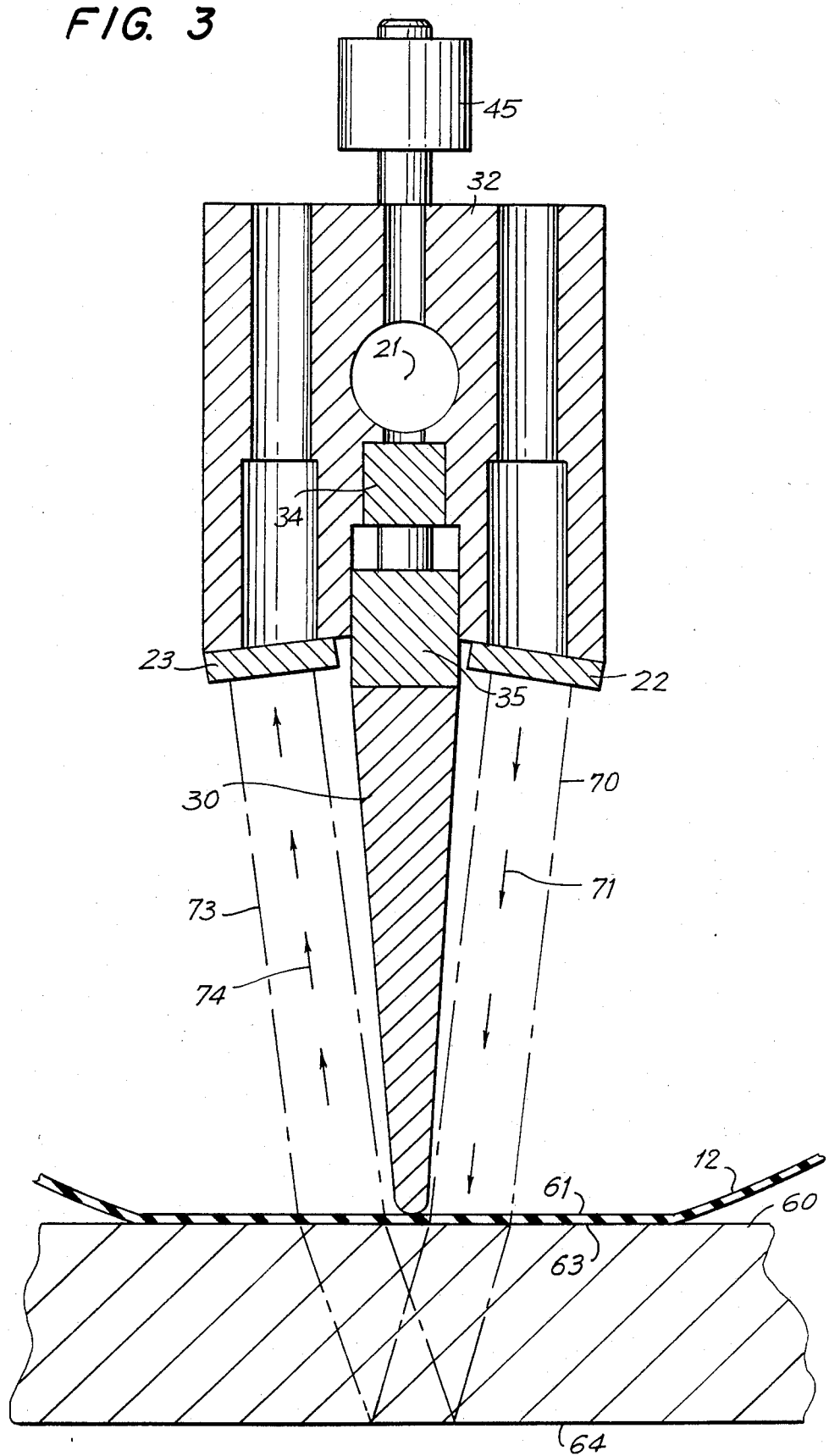

ULTRASONIC WHEEL PROBE WITH ACOUSTIC BARRIER

BACKGROUND OF THE INVENTION

This invention relates generally to ultrasonic testing systems, and more particularly, to an ultrasonic wheel detector for rolling along a specimen to be tested for flaws having a plurality of ultrasonic acoustic transducers and an acoustic barrier emersed in a coupling fluid.

The prior art has thrust at the problem of ultrasonically testing long specimens of metal objects by providing ultrasonic acoustic wheel probes which are filled with a coupling fluid and which roll along the specimen to be tested. One early ultrasonic wheel probe is described in U.S. Pat. No. 3,628,375 which issued to the applicant herein on Dec. 21, 1971. The structure described in this reference utilizes an ultrasonic transducer immersed in the coupling fluid within the annular container which forms a wheel. The ultrasonic transducer is adjustably mounted so as to be obliquely movable to control its inclination and consequently the angle of incidence of the ultrasonic energy with respect to the plane normal to the surface of the material against which the wheel is rolling. In this known system, the transducer is of the type which converts electrical signals into acoustic energy which is propagated through the coupling fluid and into the specimen being tested for flaws, and receives reflected acoustic energy which is converted back to electrical signals. It is a characteristic of such a single transducer system that considerable interface echoes are received, thereby reducing the resolution capability of the system, which in turn results in a system unable to inspect 100% of the thickness of the material under test.

The use of dual transducers, one for transmitting ultrasonic energy and the other for receiving the echoes, without an interface echo, allows the system to test and gate a specimen completely from the front surface of the specimen all the way to the back wall of the specimen material. It is, however, a problem with the use of dual transducers within a wheel filled with coupling fluid that the acoustic energy will propagate through the coupling fluid from the transmitting transducer to the receiving transducer, directly. This results in objectionable crosstalk which adversely affects the detection process. A dual transducer system, however, provides the advantage that the return echoes are received on a propagation axis which is away from the transmission axis along which is propagated the main excitation pulse. Also the returning echo to the receiver transducer is that of a boundary reflection beyond the front surface of the specimen under test.

Dual transducer testing systems are described in U.S. Pat. Nos. 4,165,648 and 4,174,636 which issued to the applicant herein on Aug. 28, 1979, and Nov. 20, 1979, respectively. In each of these known systems, isolation between the transmitting and receiving transducers is achieved by providing a separate fluid coupled wheel for each. The wheels are coupled to one another by an adjustable coupling arrangement which permits variation of the spacing between the wheels. In this manner, the dual wheel system can be adapted to accommodate specimens to be tested having different thicknesses. Inter-wheel spacing is adjusted automatically by a servo system which is responsive to a thickness-measuring transducer. The ability to use two separate wheels in dual mode operation is possible because the waves propagating through the test piece are in sheer mode allowing much steeper return angles than exist in a longitudinal mode of operation. Clearly, this known arrangement is complex and expensive. Also this known arrangement is limited to a shear wave transducer mode. It is impossible to use two fluid coupled wheels in a longitudinal mode of operation due to the physical dimensions required.

It is, therefore, an object of this invention to provide an ultrasonic wheel probe which is inexpensive and which can introduce ultrasonic acoustic energy into an elongated specimen to be tested for flaws or to determine thickness.

It is another object of this invention to provide an ultrasonic probe which can receive ultrasonic acoustic energy echoes from a specimen being tested for flaws.

It is also an object of this invention to provide an ultrasonic probe wherein transmitted ultrasonic acoustic energy is transmitted and echoes thereof are received via a confined liquid transmission medium interposed between a specimen being tested and the transmitting and receiving transducers.

It is a further object of this invention to provide a liquid immersion wheel probe wherein crosstalk communication between transmitting and receiving transducers via the liquid transmission medium is prevented.

It is additionally an object of this invention to provide an immersion-type ultrasonic probe wherein the liquid transmission medium is confined in a deformable container which is deformed in response to changes in the contour of the specimen being tested for flaws.

It is still a further object of this invention to provide an immersion-type wheel probe wherein crosstalk communication between transmitting and receiving transducers through the liquid medium is prevented notwithstanding deformation of the deformable container.

It is still another object of this invention to provide a fluid-filled acoustic wheel probe wherein changes in the distance between the transducers and a surface of the specimen being tested for flaws are monitored.

It is yet still an additional object of this invention to provide a wheel probe wherein the orientation of the transducers with respect to the specimen being tested for flaws is adjustable to permit testing of specimens of various thicknesses.

It is yet a further object of this invention to provide an ultrasonic acoustic probe wherein return echoes are propagated through a transmission medium along a different propagation axis than the original transmission.

It is yet a still further object of this invention to provide an acoustic testing arrangement using dual wheels and having improved accuracy and an increase in the testing range within a given specimen thickness.

Another object of the invention is to provide an ultrasonic wheel probe wherein transmitting and receiving transducers can be oriented to focus at a depth within the specimen being tested where flaws are suspected to be incurred.

Another additional object of the invention is to provide an acoustic probe system wherein normal echoes from the surface of the specimen being tested are monitored to determine a distance between a transducer and the surface.

An additional object of the invention is to provide an electronic gating system responsive to surface echoes from the specimen being tested for flaws and which monitors the actual transducer position in relation to the surface of the specimen.

An additional object of the present invention is to provide an ultrasonic acoustic probe arrangement having a high signal-to-noise ratio between plural transducers.

Additionally, it is an object of this invention to provide an ultrasonic acoustic wheel probe having separate transmit and received transducers.

Also, it is an object of this invention to provide an ultrasonic acoustic wheel probe arrangement which can couple dryly to specimens to be tested for flaws.

SUMMARY OF THE INVENTION

The foregoing and other objects are achieved by the present invention which provides an ultrasonic inspection wheel probe of the type having a container having a substantially annular outer surface for rotating about an axis of rotation and rolling on a specimen to be tested. The container is provided with a yoke arranged at least partially on the axis of rotation, and is filled with a coupling fluid for propagating ultrasonic acoustic energy. In accordance with the invention, the ultrasonic inspection wheel probe is provided with first and second transducer elements for transmitting acoustic energy through the coupling fluid and for receiving echoes of the ultrasonic acoustic energy, respectively. The transmitting transducer causes acoustic ultrasonic energy to propogate through the coupling fluid, the outer surface of the container, and into the specimen to be tested for flaws. An acoustic barrier is interposed between the transmitting and receiving transducers, and immersed in the coupling fluid, for isolating the receiving and transmitting transducers.

In a preferred embodiment of the invention, the acoustic barrier is mounted on the yoke so as to extend substantially to an annular inner surface of the container, thereby almost completely sealing the transducers from one another. However, the acoustic barrier is installed on the yoke using a resilient, sliding arrangement which permits the distance between the axis of rotation of the container and the outermost extent of the acoustic barrier to be reduced. This is necessary to accommodate for deformation of the container as it is rolled along the surface of the specimen to be tested. Thus, if the contour of the specimen being tested requires a deformation of the generally annular outer surface of the container or wheel, then the acoustic barrier can be retracted somewhat to accommodate for such deformation. During such retraction, however, the acoustic barrier is maintained in its predetermined alignment between the transmitting and receiving transducers. Preferably, a major plane of the acoustic barrier is coincident with a radius of the annular container.

In one embodiment of the invention, the transmitting and receiving transducers can be angled within the container so as to permit focusing at a substantially predeterminable depth within the specimen being tested. Each transducer is preferably of the type which has an axis of propagation of the acoustic energy, and the axis of each such transducer, on either side of the acoustic barrier, is generally parallel with the major plane of the acoustic barrier. Thus, the transmitted acoustic energy is propagated through the coupling fluid in a direction which is substantially parallel to, and on one side of, the major plane of the acoustic barrier; which transmitted acoustic energy enters the specimen and is reflected back along the other side of the acoustic barrier to the receiving transducer. In a preferred embodiment, each transducer is of the type which can selectably transmit or receive acoustic energy, and therefore the wheel probe is not limited to any particular direction of travel.

In accordance with a highly advantageous embodiment of the invention, a third transducer is provided which performs both the transmitting and receiving functions. This third transducer is arranged to transmit its acoustic energy directly to the back of the acoustic barrier, in a direction parallel, and substantially coincident with, the major plane of the acoustic barrier. Thus, a reflection from the acoustic barrier to this third transducer is responsive to the position of the acoustic barrier as it is retracted and extended in accordance with the deformation of the annular outer surface of the container. Thus, the position of the acoustic barrier can be monitored.

In accordance with the invention, feedback triggering circuitry can be coupled to the third transducer so as to define time periods during which echoes resulting from defects within the specimen being tested can be expected to be incurred. This function can be performed by gating circuitry which is responsive to the feedback triggering circuits, and which can be arranged to eliminate any boundry reflections, thereby removing the need to gate out interface reflections which would otherwise reduce the material thickness that could be tested. Such a self-adjusting system allows critical segments of the specimen to be tested with high measurement reliability.

It is to be noted that the invention herein is not limited to unitary transmit and receive transducers, but each such transducer may be replaced by a plurality of transducers in the form of an array. Such an array of transducers would extend the area of coverage during testing. The use of such arrays, when coupled with the ability of each transducer to be angled individually, results in an advantageous capability wherein various materials having different configurations can be tested. Additionally, a selection of an appropriate transducer wheel membrane material, such as a silicone rubber or a low durometer polyurethane, combined with a separate transducer, or array of transducers, for the transmit and receive functions, enables the use of much higher transmission powers, without the need to contend with artifact echoes, thereby allowing dry coupling inspection of material. The present invention, therefore, provides the significant advantage that ultrasonic inspection of gas transmission pipelines can be achieved without the introduction of any fluids within the pipeline. Thus, the need for inspecting gas pipelines without the introduction of any fluids therein is satisfied.

BRIEF DESCRIPTION OF THE DRAWINGS

Comprehension of the invention is facilitated by reading the following detailed description in conjunction with the annexed drawings, in which:

FIG. 3 is a cross-sectional side view of the embodiment of FIG. 1 showing radial displacement of the acoustic barrier and ultrasonic energy beam paths.

DETAILED DESCRIPTION

Figure 1:
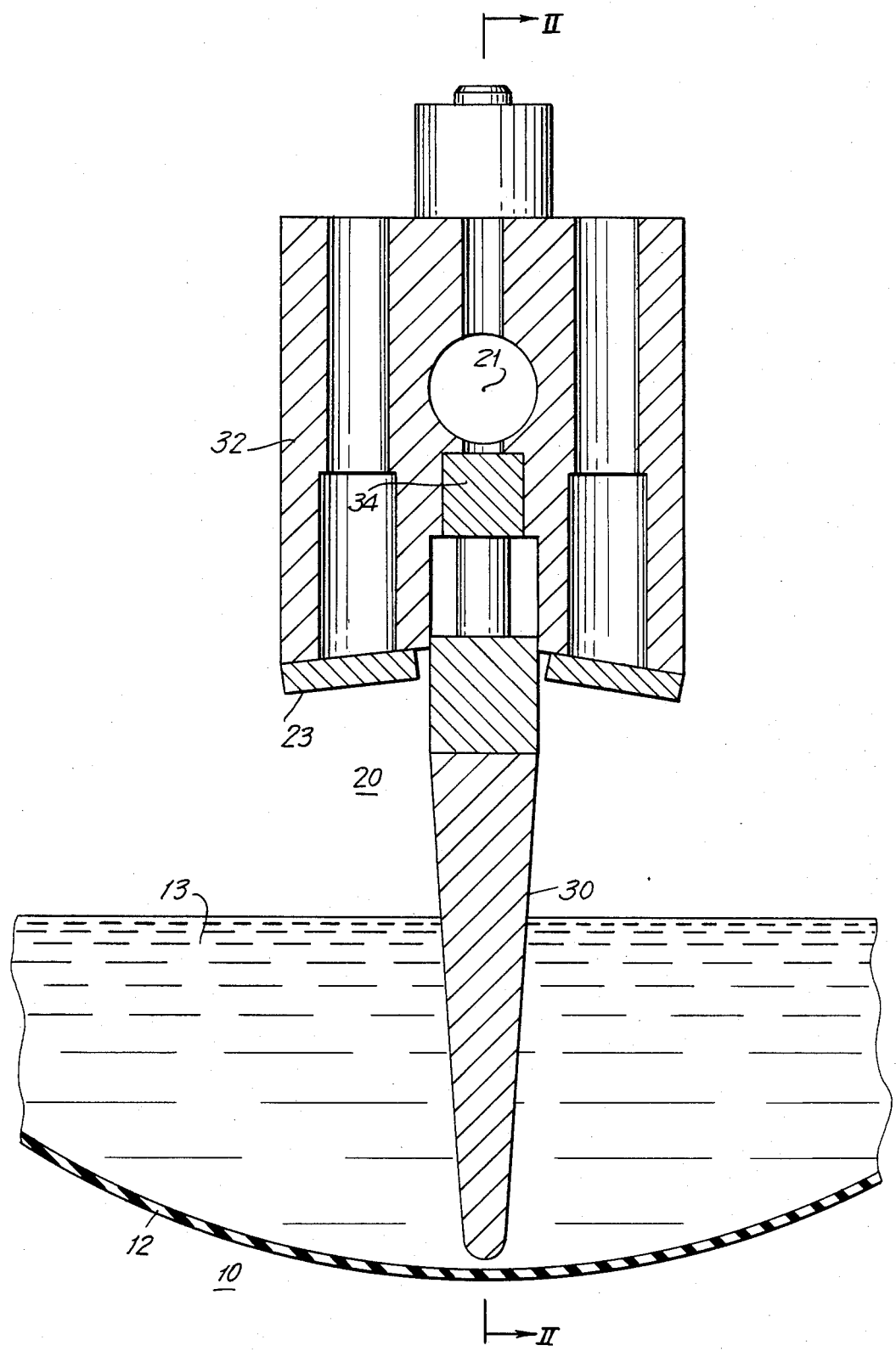
FIG. 1 is a cross-sectional side view of one embodiment of the invention.

FIG. 1 is a cross-sectional side view of a wheel probe arrangement 10 constructed in accordance with the principles of the invention. As shown in this figure, a wheel membrane material 12 is arranged to encircle a transducer assembly 20 concentrically about an axis of rotation 21 which is shown in this cross-sectional view as a point.

Wheel membrane material 12 may be formed, in certain embodiments, of a silicone rubber or a low durometer polyurethane which can couple acoustically with a specimen to be tested, as will be described hereinbelow, without need of an external coupling fluid. Wheel membrane material 12 has an annular configuration so as to define a space therein containing a coupling fluid 13. In a preferred embodiment, the entire volume within the wheel membrane material is filled with the coupling fluid, and therefore transducer assembly 20 is immersed in the coupling fluid.

Transducer assembly 20 is shown to have first and second transducers 22 and 23, respectively. In this embodiment, each of the first and second transducers is of the type which can convert electrical energy into ultrasonic acoustic energy, for transmitting the ultrasonic acoustic energy, and which can receive the ultrasonic acoustic energy and convert it into electrical energy. Such transducers are of a known type and will not be described here in detail.

FIG. 1 further shows an acoustic barrier 30 arranged substantially radially with respect to axis of rotation 21 and interposed between first and second transducers 22 and 23. The acoustic barrier is installed onto a yoke 32 of transducer assembly 20. The particular mounting arrangement used in the present embodiment for coupling the acoustic barrier to the yoke will be discussed hereinbelow with respect to FIG. 2.

FIG. 1 further shows a third transducer 34 which, in this embodiment, is arranged intermediate of acoustic barrier 30 and axis of rotation 21. Third transducer 34 is of the type which can transmit and receive acoustic energy and is arranged to receive reflection from a barrier mounting member 35. As will be described hereinbelow, acoustic barrier 30, and its associated barrier mounting member 35 are movable radially with respect to axis of rotation 21. This motion is monitored by third transducer 34 so that an electrical signal is produced responsive to the radial location of the acoustic barrier, and consequently, as will be described hereinbelow, the distance between transducers 22 and 23 and the surface of a specimen to be tested (not shown in this figure).

Figure 2:
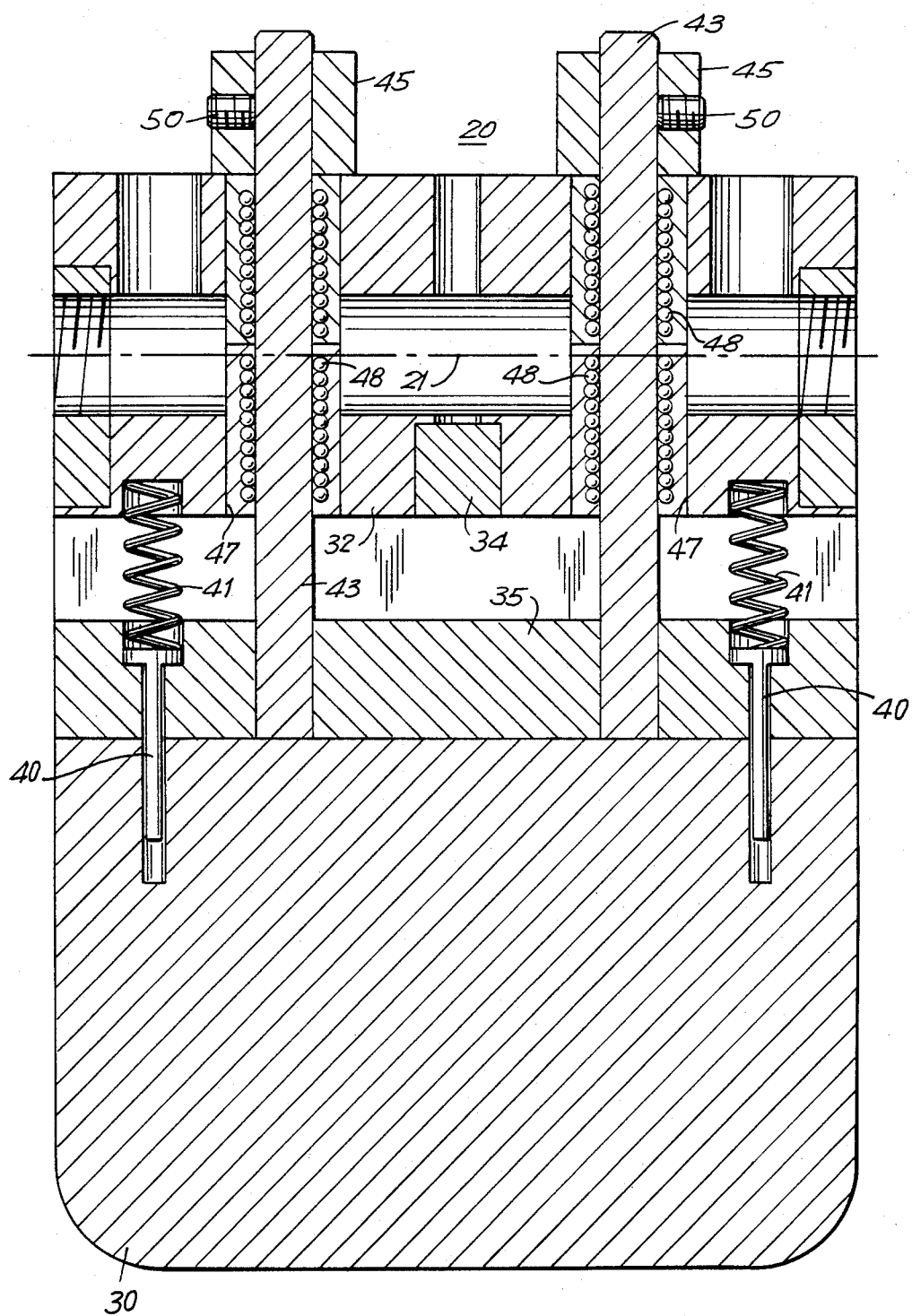
FIG. 2 is a cross-sectional end view of the embodiment of FIG. 1 taken along line II—II.

FIG. 2 is a cross-sectional view of the embodiment of FIG. 1 taken along line II—II. As shown in FIG. 2, acoustic barrier 30 of transducer assembly 20 is coupled to barrier mounting member 35 by a pair of coupling devices 40 which, in this embodiment, may be screws. As shown, coupling devices 40 are countersunk into barrier mounting member 35. The countersunk holes in barrier mounting member 35 accommodate springs 41 which urge the barrier mounting member downwardly away from yoke 32. However, complete separation of barrier mounting member 35 from the yoke is prevented by a pair of shafts 43 which extend through the yoke and are terminated at their upper ends with nuts 45.

Shafts 43 slide through holes 47 which pass through yoke 32. A plurality of bearings 48 permit linear travel of shafts 43 through holes 47 while maintaining a substantially radial alignment of acoustic barrier 30. To prevent nuts 45 from loosening off of shafts 43, each such nut is provided with a locking screw 50. Each of nuts 45 is secured at a location along shafts 43 such that a predetermined distance is provided between axis of rotation 21 and the lowermost extent of acoustic barrier 30. However, this distance may be shortened by the application of a force sufficient to compress resilient springs 41. During such movement of the acoustic barrier, a predetermined alignment is maintained by the communication of shafts 43 with bearings 48.

FIG. 3 is a cross-sectional representation of the embodiment of FIGS. 1 and 2 showing wheel membrane material 12 deformed at its lowermost extent by communication with a specimen 60 to be tested. The deformation of wheel membrane material 12 in its region 61 where the wheel membrane material communicates with specimen 60, causes a force to be applied upward through acoustic barrier 30 so as to reduce the distance between axis of rotation 21 and the lowermost extent of acoustic barrier 30. The application of such a force causes barrier mounting member 35 to come closer to third transducer 34 and nut 45 to be raised off of yoke 32. Thus, the lowermost extent of acoustic barrier 30 tracks the deformation of wheel membrane material 12.

As shown in FIG. 3, first transducer 22 transmits a beam of ultrasonic acoustic energy 70 substantially along an axis of propagation 71. Beam of ultrasonic acoustic energy 70 impinges upon a surface 63 of specimen 60 and is refracted. The beam continues to propagate through the specimen until it reaches a back surface 64 where it is reflected as an echo beam 73 substantially along an axis of propagation 74. In a preferred embodiment of the invention, transducers 22 and 23 are installed onto yoke 32 by means (not shown) which permits tilting of the transducers so as to permit the beam of ultrasonic acoustic energy and the echo beam to be directed, as desired. Generally, the beams of ultrasonic acoustic energy are directed so as to be substantially parallel to the surfaces of acoustic barrier 30. The portion of beam of ultrasonic energy 70 which is reflected from surface 63 of specimen 60 is prevented from reaching second transducer 23 by the interposition of acoustic barrier 30.

Although the invention has been described in terms of specific embodiments and applications, persons skilled in the art, in light of this teaching, can generate additional embodiments without exceeding the scope or departing from the spirit of the claimed invention. Accordingly, it is to be understood that the drawings and descriptions in this disclosure are proffered to facilitate comprehension of the invention and should not be construed to limit the scope thereof.

What is claimed is:

1. An ultrasonic inspection apparatus of the type having a container having a substantially annular outer surface for rotating about an axis of rotation and rolling on a specimen to be tested, the container having a yoke arranged at least partly on the axis of rotation and being filled with a coupling fluid for propagating ultrasonic acoustic energy, the ultrasonic inspection apparatus comprising:

first and second transducer means for transmitting ultrasonic acoustic energy through the coupling fluid, the substantially annular outer surface of the container, and into the specimen to be tested, and for receiving echoes of said transmitted ultrasonic acoustic energy, respectively; and acoustic barrier means interposed between said first and second transducer means and immersed in the coupling fluid for acoustically isolating said first transducer means from said second transducer means, wherein there is further provided mounting means for securing said acoustic barrier means to the yoke, said acoustic barrier means extending substantially to an annular inner surface of the container, said annular inner surface being in communication with the coupling fluid.

2. The ultrasonic inspection apparatus of claim 1 wherein said mounting means further comprises resilient means for extending an outermost extent of said acoustic barrier means substantially to said annular inner surface of the container and for permitting a reduction in a distance between the yoke and said outermost extent of said acoustic barrier means in response to a deformation of the annular outer surface.

3. The ultrasonic inspection apparatus of claim 2 wherein there is further provided alignment means for maintaining an alignment of said acoustic barrier means with respect to the yoke as said distance between the yoke and said outermost extent of said acoustic barrier means is reduced.

4. The ultrasonic inspection apparatus of claim 1 wherein said first and second transducer means are arranged to transmit and receive the ultrasonic acoustic energy along respective axes of propagation, said axes being substantially parallel to a surface of said acoustic barrier means.

5. The ultrasonic inspection apparatus of claim 2 wherein there is further provided third transducer means arranged to transmit ultrasonic acoustic energy and receive echoes of said transmitted ultrasonic acoustic energy, said third transducer means being arranged to transmit said ultrasonic acoustic energy along an axis which extends through said acoustic barrier means.

6. The ultrasonic inspection apparatus of claim 5 wherein said third transducer means is arranged to transmit ultrasonic acoustic energy to said acoustic barrier means and receive echoes therefrom so as to monitor the location of said acoustic barrier means.

7. The ultrasonic inspection apparatus of claim 6 wherein said third transducer means is located intermediate of the axis of rotation and said acoustic barrier means.

8. The ultrasonic inspection apparatus of claim 5 wherein there is further provided feedback triggering means coupled to said third transducer means for defining a moment of time after which echoes responsive to flaws within the specimen being tested are expected to be received by said second transducer means.

9. The ultrasonic inspection apparatus of claim 8 wherein there is further provided gate circuit means having first and second transmission states responsive to said feedback triggering means for transmitting signals responsive to echoes received after said moment of time, and impeding signals responsive to echoes received before said moment of time.

10. The ultrasonic inspection apparatus of claim 9 wherein said signals responsive to echoes received before said moment of time correspond to interface echoes reflected from a surface of the specimen to be tested.

11. An ultrasonic wheel probe having a wheel-shaped container for rolling on a specimen and for containing a coupling fluid, said ultrasonic wheel probe having a yoke arranged in the vicinity of an axis of rotation, the ultrasonic wheel probe further comprising:
    a plurality of ultrasonic transducers for transmitting and receiving ultrasonic acoustic energy propagating through the coupling fluid; and
    barrier means extending substantially radially with respect to the axis of rotation, said barrier means being displaceable along said substantially radial extent in response to the contour of the specimen.

12. The ultrasonic wheel probe of claim 11 wherein there is further provided monitoring means for monitoring said displacement of said barrier means.

13. The ultrasonic wheel probe of claim 12 wherein said monitoring means comprises ultrasonic transducer means for communicating ultrasonically with said barrier means.

14. The ultrasonic wheel probe of claim 13 wherein there is further provided mounting means for displaceably coupling said barrier means to the yoke.

15. The ultrasonic wheel probe of claim 14 wherein said ultrasonic communication between said monitoring means and said barrier means occurs via said mounting means.

16. The ultrasonic wheel probe of claim 14 wherein said mounting means further comprises alignment means for permitting said displacement of said barrier means while maintaining said substantially radial extension orientation of said barrier means.

17. The ultrasonic wheel probe of claim 16 wherein said alignment means further comprises:
    shaft means for engaging with the yoke; and
    bearing means for facilitating axial displacement of said shaft means.

18. The ultrasonic wheel probe of claim 17 wherein there is further provided stop means coupled to said shaft means for limiting a maximum radial extent of said barrier means.

19. A method of detecting flaws in a specimen, the method comprising the steps of:
    transmitting a beam of ultrasonic acoustic energy through a coupling fluid along a predetermined path of transmission and into the specimen;
    conducting a beam of reflected ultrasonic acoustic energy along a predetermined echo path;
    interposing an acoustic barrier between said predetermined path of transmission and said predetermined echo path; and
    displacing said acoustic barrier along a predetermined displacement path in response to a contour of the specimen.

20. The method of claim 19 wherein there is provided the further step of monitoring said displacement of said acoustic barrier along said predetermined displacement path.

21. The method of claim 20 wherein said step of monitoring comprises the step of transmitting a further beam of ultrasonic acoustic energy substantially along said predetermined displacement path toward said acoustic barrier.

22. The method of claim 19 wherein there is provided the further step of interposing a substantially annular, deformable membrane between said acoustic barrier and the specimen.

23. The method of claim 22 wherein there is provided the further step of moving said deformable membrane in a direction which is substantially orthogonal to said predetermined displacement path.

* * * * *